United States Patent
Nozaki et al.

(10) Patent No.: US 11,519,892 B2
(45) Date of Patent: Dec. 6, 2022

(54) PRECISION AGRICULTURE SUPPORT SYSTEM AND PRECISION AGRICULTURE SUPPORT METHOD

(71) Applicants: Shinji Nozaki, Kanagawa (JP); SaraniaSat, Inc., Tujunga, CA (US)

(72) Inventors: Shinji Nozaki, Kanagawa (JP); Thomas George, Tujunga, CA (US)

(73) Assignees: Shinji Nozaki, Kanagawa (JP); SARANIASAT, INC, Tujunga, CA (US)

( * ) Notice: Subject to any disclaimer, the term of this patent is extended or adjusted under 35 U.S.C. 154(b) by 335 days.

(21) Appl. No.: 16/839,301

(22) Filed: Apr. 3, 2020

(65) Prior Publication Data
US 2020/0386733 A1 Dec. 10, 2020

(30) Foreign Application Priority Data
Jun. 5, 2019 (JP) .............................. JP2019-105490

(51) Int. Cl.
*G01N 33/00* (2006.01)
*G01N 21/3581* (2014.01)
(Continued)

(52) U.S. Cl.
CPC .......... *G01N 33/0098* (2013.01); *A01G 7/00* (2013.01); *A01M 7/0089* (2013.01); *G01J 5/00* (2013.01);
(Continued)

(58) Field of Classification Search
CPC .... G01N 33/0098; A01G 7/00; A01M 7/0089
See application file for complete search history.

(56) References Cited

U.S. PATENT DOCUMENTS

2004/0212804 A1 10/2004 Neff et al.
2015/0177429 A1 6/2015 Darty
(Continued)

FOREIGN PATENT DOCUMENTS

CN 108982408 12/2018
JP 2003-279415 10/2003
(Continued)

OTHER PUBLICATIONS

Notice of Reasons for Refusal dated Jan. 27, 2021 in corresponding Japanese Patent Application No. 2019-105490 with English-language translation.
(Continued)

*Primary Examiner* — Hugh Maupin
(74) *Attorney, Agent, or Firm* — Wenderoth, Lind & Ponack, LLP

(57) ABSTRACT

A precision agriculture support system is provided with a measuring device, a storage device and a plant species determining unit. The measuring device measures a first spectral characteristic of light derived from vegetation in a support target area. The storage device stores a database of spectrum according to species that shows a spectral characteristic of a desired crop. The plant species determining unit determines whether a plant included in the vegetation is the desired crop or not based on the database of spectrum according to species and a measurement result of the first spectral characteristic. The plant species determination unit further carries out distinction of agricultural crops, distinction of agricultural crops and weeds and the like. Furthermore, the precision agriculture support system identifies an area where abnormality is occurring, estimates a nature of the abnormality and carries out an early warning by providing a countermeasure against the abnormality.

12 Claims, 12 Drawing Sheets

(51) Int. Cl.
  *G01N 21/3563* (2014.01)
  *A01G 7/00* (2006.01)
  *A01M 7/00* (2006.01)
  *G01J 5/00* (2022.01)
  *G01J 5/80* (2022.01)

(52) U.S. Cl.
  CPC ..... *G01N 21/3563* (2013.01); *G01N 21/3581* (2013.01); *G01J 5/80* (2022.01)

(56) References Cited

U.S. PATENT DOCUMENTS

| | | |
|---|---|---|
| 2017/0371079 A1 | 12/2017 | Darty |
| 2018/0275325 A1 | 9/2018 | Darty |
| 2020/0110208 A1 | 4/2020 | Darty |
| 2020/0240841 A1* | 7/2020 | McQuilkin ............... G01J 3/12 |
| 2020/0294620 A1* | 9/2020 | Bauer ............... G01N 33/0098 |

FOREIGN PATENT DOCUMENTS

| | | |
|---|---|---|
| JP | 2006-524343 | 10/2006 |
| JP | 2009-58333 | 3/2009 |
| JP | 2013-145507 | 7/2013 |
| JP | 2015-77113 | 4/2015 |
| JP | 5910018 | 4/2016 |
| JP | 2016-165303 | 9/2016 |
| JP | 5991182 | 9/2016 |
| JP | 6064712 | 1/2017 |
| JP | 2019-23646 | 2/2019 |

OTHER PUBLICATIONS

Harrison et al., "Classification of tree species based on longwave hyperspectral data from leaves, a case study for a tropical dry forest", Int J Appl Earth Obs Geoinformation, 2018, vol. 66, pp. 93-105.

Buitrago et al., "Connecting infrared spectra with plant traits to identify species", ISPRS Journal of Photogrammetry and Remove Sensing, Mar. 2018, vol. 139, pp. 183-200.

* cited by examiner

PRECISION AGRICULTURE SUPPORT SYSTEM AND PRECISION AGRICULTURE SUPPORT METHOD

TECHNICAL FIELD

The present invention relates to a precision agriculture support system and a precision agriculture support method by use of this precision agriculture support system.

BACKGROUND ART

Aiming to increase production, improve quality, reduce costs and the like in agricultural crops, it is expected to use advanced technologies such as robot technology, big data, artificial intelligence, Internet of Things (IoT) in agriculture. Such agriculture is called "precision agriculture", "smart agriculture" or the like.

To understand a state of plants in detail, optical remote sensing can be carried out by use of drones, aircrafts, balloons, artificial satellites or the like provided with a measurement device. By using a so-called hyperspectral camera as this measurement device, it is possible to acquire more detailed data than an image obtained by simply photographing plants. For example, it is also possible to automatically identify a type of plants included in a wide range of vegetation without relying on visual inspection by an experienced expert.

In relation with the above, patent literature 1 (Japanese Patent Publication No. 5910018 B) discloses an invention of a program, information processing method and apparatus for specifying plant species. In the invention of the patent literature 1, reflection spectrum from trees is measured by a hyperspectral camera, a result of this measurement is compared with reference spectrum of trees to be distinguished and tree species is identified based on their similarity. Herein, spectrum band used in the measurement is a band with wavelength of 400 nm or more and 900 nm or less included in bands of visible rays and near-infrared rays, excluding a part of band in which influence of change in chlorophyll content appears.

In addition, a patent literature 2 (Japanese patent publication No. 5991182 B) discloses an invention of plant species determination program, plant species determination method and plant species determination apparatus. In the invention of the patent literature 2, spectrum of tree is measured by use of a hyperspectral camera, a matching between a result of this measurement and mixed spectral data is carried out and tree species are determined based on their similarity. Herein, a spectral band used for the matching is a band with wavelength of 400 nm or more and 1050 or less, included in bands of visible rays and near-infrared rays. In addition, the mixed spectral data are generated based on tree spectral data and soil spectral data.

In addition, a patent literature 3 (Japanese patent publication No. 6064712 B) discloses an invention of tree species identification apparatus and tree species identification method. In the invention of the patent literature 3, reflection spectrum from trees is measured by use of a hyperspectral camera, a result of this measurement is compared with reference spectral data of each tree and tree species is determined based on their similarity. Herein, even in a case where spectra of two different trees are mixed in one pixel included in the spectral data, species of mixed trees can be determined by use of mixed reference spectral data in which reference spectral data of two species of trees are mixed with a predetermined mixing ratio.

CITATION LIST

Patent Literature

[Patent Literature 1] Japanese patent publication No. 5910018 B
[Patent Literature 2] Japanese patent publication No. 5991182 B
[Patent Literature 3] Japanese patent publication No. 6064712 B

SUMMARY OF INVENTION

Problem to be Solved by Invention

In the series of inventions disclosed in patent literatures 1 to 3, spectrum in bands from visible rays to near-infrared rays of the reflected light from trees is measured by used of a hyperspectral camera. And, a result of this measurement is compared with reference spectral data to determine species of trees. However, in this measurement, among bands from visible rays to near-infrared rays, a part of band in which influence of change in chlorophyll content appears is excluded. In other words, in the series of inventions disclosed in the patent literatures 1 to 3, in order to determine species of trees, change of state of the trees is intentionally ignored. Therefore, in the series of inventions disclosed in the patent literatures 1 to 3, change of growing state of the trees cannot be known. In addition, the patent literatures 1 to 3 disclose only determination of type of trees among determinations of species of plants in fact. And, areas excluded from the range of wavelength of measurement in the patent literatures 1 to 3 may be useful to determine species of agricultural crops other than trees, such as cereals, and may be useful to distinguish between agricultural crops such as cereals and unwanted weeds.

Precision agriculture that grows desired agricultural crops will be supported by use of remote sensing. Other problems and new features will be apparent from disclosures of this description and attached drawings.

Means for Solving the Problems

Means for solving the problems will be described below with symbols used in "Description of Embodiments". Those symbols are added in order to clarify relationship between description of "Claims" and "Description of Embodiments". However, those symbols are not to be used in interpretation of technical scope of the invention described in "Claims".

According to an embodiment, a precision agriculture support system (1) is provided with a measuring device (7), a storage device (5) and a plant species determining unit (41). The measuring device (7) measures a first spectral characteristic of light derived from a vegetation in a support target area. The storage device (5) stores a database of spectrum according to species (51) that shows a feature a spectral characteristic of a desired crop has. The plant species determining unit (41) determines whether a plant included in the vegetation is the desired crop or not based on the database of spectrum according to species (51) and a measurement result of the first spectral characteristic. The desired crop includes rice plant.

According to an embodiment, a precision agriculture support method includes preparing a database of spectrum according to species (51) that shows a feature a spectral characteristic of a desired crop has, carrying out a measurement of a spectral characteristic of light derived from a vegetation in a support target area (S11) and determining whether a plant included in the vegetation is the desired crop or not based on the database of spectrum according to species (51) and a result of the measurement (S12). The desired crop includes rice plant.

Effect of Invention

According to an embodiment described as above, a precision agriculture of growing desired crop can be supported by remote sensing.

BRIEF DESCRIPTION OF DRAWINGS

FIG. 7C is a diagram in which FIG. 7A and FIG. 7B are combined.

DESCRIPTION OF EMBODIMENTS

An embodiment of a precision agriculture support system and a precision agriculture support method according to the present invention will be described below with reference to attached drawings.

First Embodiment

In the present embodiment, identification of a plant species by use of visible rays and/or infrared rays that are reflected or radiated by the plant, specifically among them mid-wavelength infrared (MWIR) band component and long-wavelength infrared (LWIR) band component, will be described.

Figure 1:
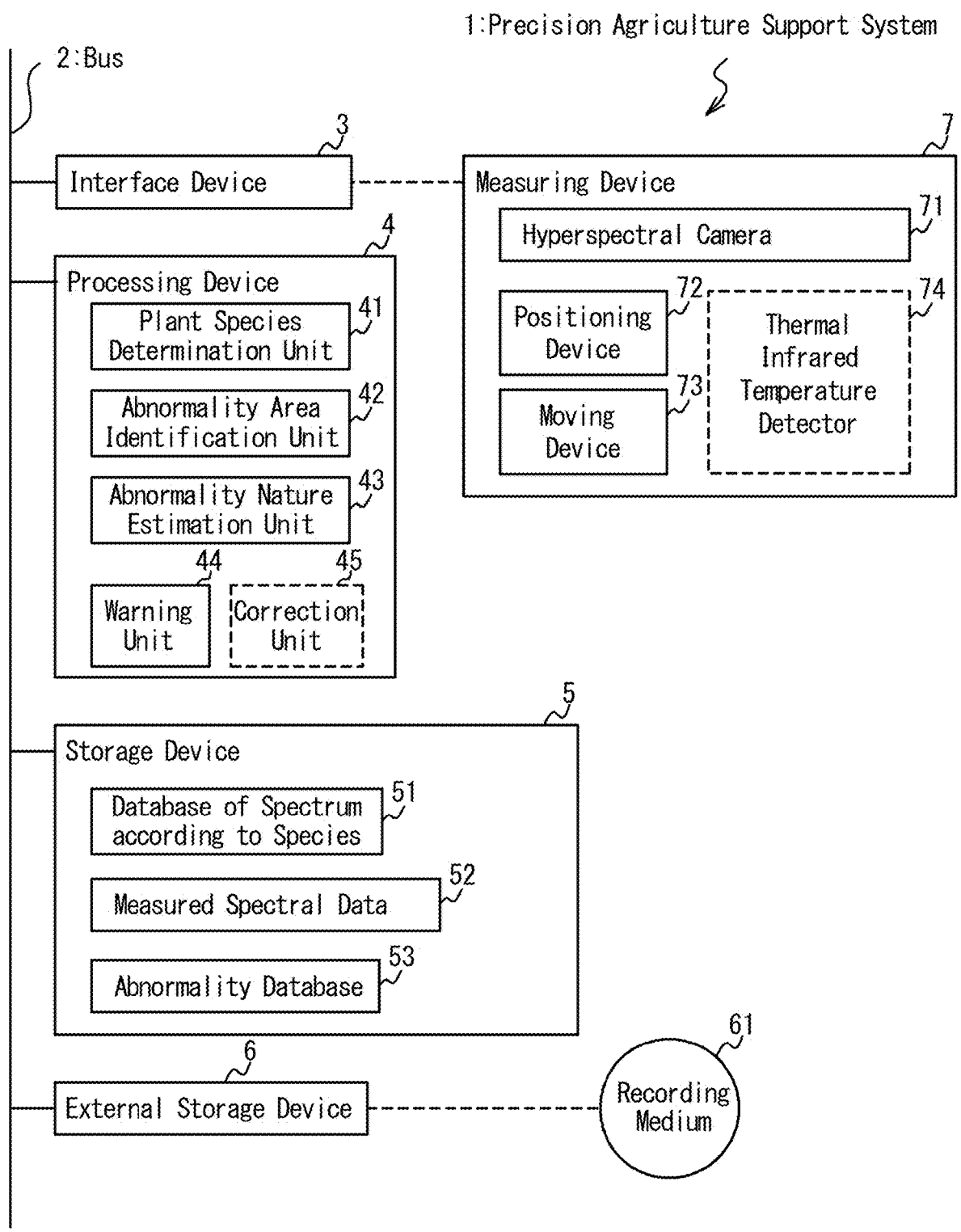
FIG. 1 is a block circuit diagram that shows a configuration example of a precision agriculture support system according to an embodiment.

A configuration example of the precision agriculture support system 1 will be described with reference to FIG. 1. FIG. 1 is a block circuit diagram that shows a configuration example of a precision agriculture support system 1 according to an embodiment.

The precision agriculture support system 1 in FIG. 1 is provided with a bus 2, an interface device 3, a processing device 4, a storage device 5, an external storage device 6 and a measuring device 7. Among those components, the bus 2, the interface device 3, the processing device 4, the storage device 5 and the external storage device 6 may be constituted as a general computer or a part thereof. That is, each of the interface device 3, the processing device 4, the storage device 5 and the external storage device 6 is connected to the bus 2 and is constituted to be electrically communicable to each other via the bus 2.

The measuring device 7 is provided with a hyperspectral camera 71, a positioning device 72 and a moving device 73. The measuring device 7 may be further provided with a thermal infrared temperature detector 74 as described later. The hyperspectral camera 71 carries out remote sensing of a measurement target. In other words, the hyperspectral camera 71 optically observes the measurement target and measures spectral characteristics related to a predetermined wavelength range including at least a part of visible light, near-infrared rays, short-wavelength infrared rays, mid-wavelength infrared rays and long-wavelength infrared rays, among a part or all of reflected light, emitted light and radiated light derived from the measurement target. In the present application, an emitted light is light that is emitted from an object when excited by sunlight. A total number of wavelength bands of which the hyperspectral camera 71 can measure spectral characteristics at a time is, in general, 100 or more. It should be noted that in case of a hyperspectral camera 71 of a type of using a spectrometer in order to vary wavelength of measurement target, a predetermined time may be required to measure spectral characteristics of a series of wavelengths. However, a hyperspectral camera 71 of a type of using a CCD detector may measure spectral characteristics of a series of wavelengths at a time. However, depending on measurement conditions, instead of a hyperspectral camera 71, a multiband sensor with a smaller total number of wavelength bands of which spectral characteristics can be measured at a time may be used and a thermal infrared (TIR) image sensor that can measure spectral characteristics with only one wavelength range of long-wavelength infrared rays at a time may be used.

On the other hand, there is a predetermined limit in an instantaneous field of view that a hyperspectral camera 71 can observe at a time. Therefore, the moving device 73 moves the hyperspectral camera 71 and/or the measurement target to appropriately adjust relative position relationship between the hyperspectral camera 71 and the measurement target. By doing so, the hyperspectral camera 71 can observe a measurement target that is larger than its instantaneous field of view. The moving device 73 may be for example an artificial satellite, a balloon, an aircraft, a drone or the like that is mounted with the hyperspectral camera 71 and moves.

The positioning device 72 measures relative position relationship between the hyperspectral camera 71 and the measurement target. This relative position relationship preferably includes a two-dimensional position information that may be defined by latitude and longitude for example, and may further include a three-dimensional position information added with a distance in a vertical direction from the target object to the hyperspectral camera 71, that is, height. A positioning result acquired by the positioning device 72 is preferably recorded in association with measurement result of spectral characteristics that is acquired by the hyperspectral camera 71 at same time. The positioning device 72 may be provided with, for example, a global positioning system (GPS) device, an acceleration sensor, a light detection and ranging (LIDAR) device or a laser imaging detection and ranging (LIDAR) device, a computer that controls those devices or the like.

Figure 2A:
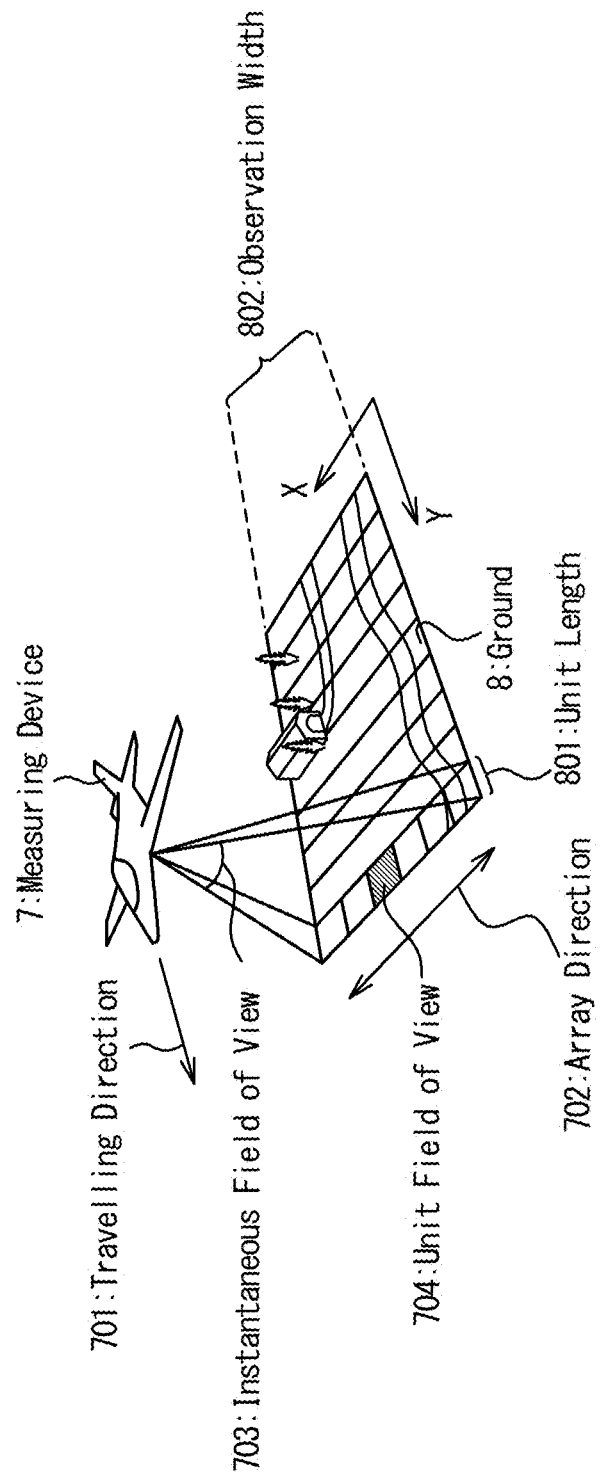
FIG. 2A is a diagram that shows an example of a method to acquire a three-dimensional spectral data in an embodiment.

A case in which the measuring device 7 is an aircraft that is mounted with a hyperspectral camera 71 having a plurality of photodetector one-dimensionally arranged and a GPS device and moves will be described with reference to FIG. 2A. In other words, a case in which the hyperspectral camera 71 has a plurality of photodetectors, the positioning device 72 is a GPS device and the moving device 73 is an aircraft will be described. FIG. 2A is a diagram that shows an example of a method to acquire a three-dimensional spectral data in an embodiment.

The aircraft, that is the moving device 73, flies in a sky over the ground 8 in a travelling direction 701 parallel to Y axis direction. Herein, the Y axis direction is, for example, a direction perpendicular to the vertical direction; however, this example is not limitative. The hyperspectral camera 71 is arranged so that light can be received from the ground 8. In the area of the ground 8, a range in which one photodetector of the hyperspectral camera 71 can observe at a time is a unit field of view 704. The plurality of photodetectors is arranged in a direction corresponding to X axis direction so that unit field of view 704 of each photodetector is adjacent in a direction of the array direction 702. By doing so, a range in which the hyperspectral camera 71 can observe at a time is enlarged to the instantaneous field of view 703 having an observation width 802 in X axis direction. Herein, X axis direction is, for example, a direction perpendicular to both the vertical direction and Y axis direction. By repeating such observation each time the aircraft as the moving device 73 advances a unit length 801 in Y axis direction and by combining observation results of the instantaneous field of view 703 on data, the spectral characteristics can be measured for a large area having the observation width 802 of the ground 8. As a result of such measurement, data called three-dimensional spectral data can be obtained.

Figure 2B:
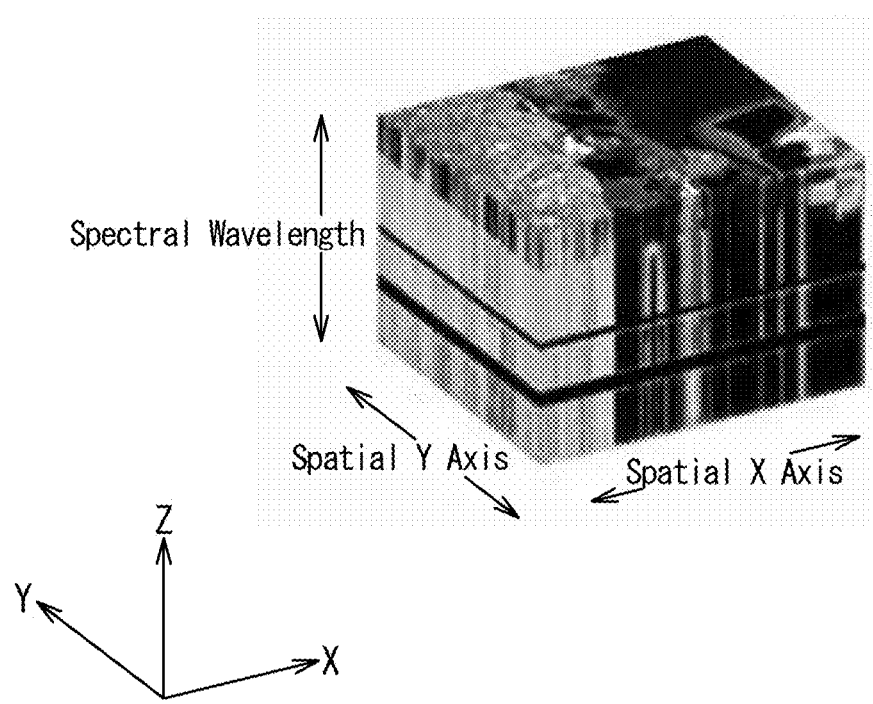
FIG. 2B is a diagram that shows an example of a three-dimensional spectral data acquired by the method in FIG. 2A.

A three-dimensional spectral data will be described with reference to FIG. 2B. FIG. 2B is a diagram that shows an example of a three-dimensional spectral data acquired by the method in FIG. 2A.

The three-dimensional spectral data in FIG. 2B has a spatial X axis, a spatial Y axis and a virtual axis of spectral wavelength. Herein, the spatial X axis and the spatial Y axis may be parallel to the array direction 702 in which the unit field of view 704 of each photodetector of the hyperspectral camera 71 is adjacent and the travelling direction 701 in which the moving device 73 moves, respectively, when the measuring device 7 observes spectral characteristics by use of the hyperspectral camera 71. In other words, the spatial X axis and the spatial Y axis in FIG. 2B may correspond to X axis and Y axis in FIG. 2A, respectively.

On the other hand, the remaining virtual axis of the spectral wavelength shows wavelength of light of which the spectral characteristics are measured. More specifically, it shows a band including the wavelength of the light of which the spectral characteristics are measured. In FIG. 2B, the spectral wavelength is shown as Z axis.

As described above, in the three-dimensional spectral data in FIG. 2B, a spectral intensity of the spectral wavelength band at an arbitrary measurement position of which the spectral characteristics are measured may be represented as a color at an intersection of corresponding X axis, Y axis and Z axis. More specifically, the spectral intensity may be represented as hue, brightness, saturation or their combination of a color. However, it is preferable that an actual three-dimensional spectral data is stored in the storage device 5 in a format of combination of measurement position coordinates, spectral wavelength band and measured value of spectral intensity.

Figure 2C:
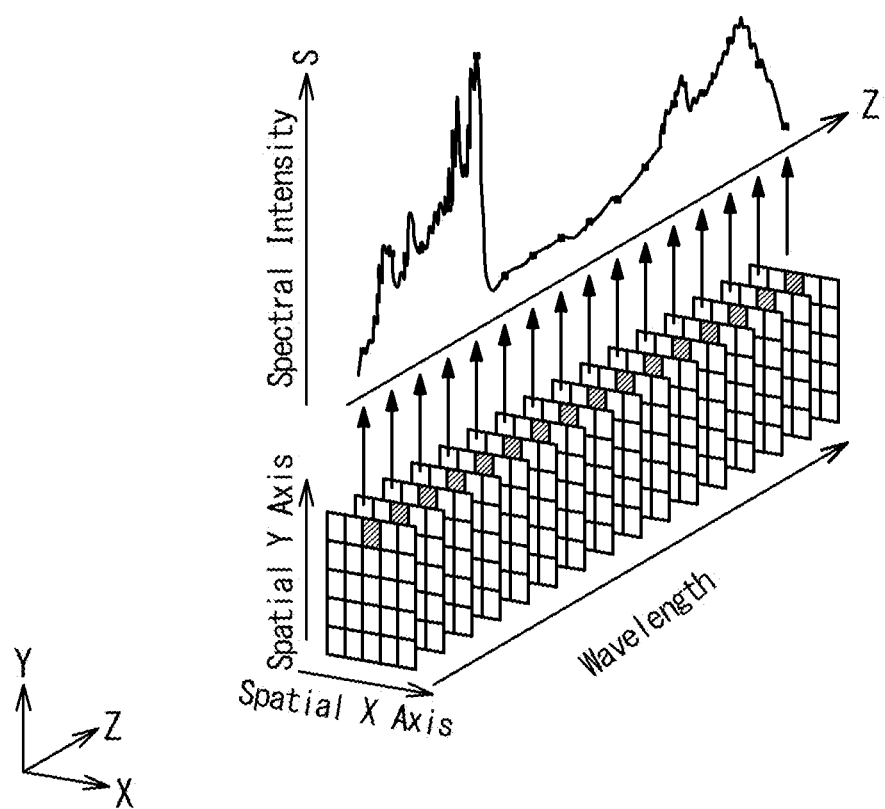
FIG. 2C is a diagram to describe a principle of extracting spectral characteristics at an arbitrary measurement position from the three-dimensional spectral data in FIG. 2B.

Extraction of spectral characteristics at an arbitrary measurement position included in measurement area from a three-dimensional spectral data will be described with reference to FIG. 2C. FIG. 2C is a diagram to describe a principle of extracting spectral characteristics at an arbitrary measurement position from the three-dimensional spectral data in FIG. 2B.

In the example in FIG. 2C, for an easier explanation, the measurement area is divided into 5 cells in the spatial X direction, 5 cells in the spatial Y direction and 25 cells in total. Those 25 cells correspond to 25 measurement positions, respectively. In addition, in correspondence with respective measurement position, wavelength is divided into 16 bands in total and measurement result of spectral intensity in respective band is recorded. By arranging a point that represents the spectral intensity defined to each band on a plane defined by S axis for spectral intensity and Z axis for wavelength and by connecting such points in order of the wavelength, the spectral characteristics at the measurement position can be represented as a waveform thereof.

Figure 3:
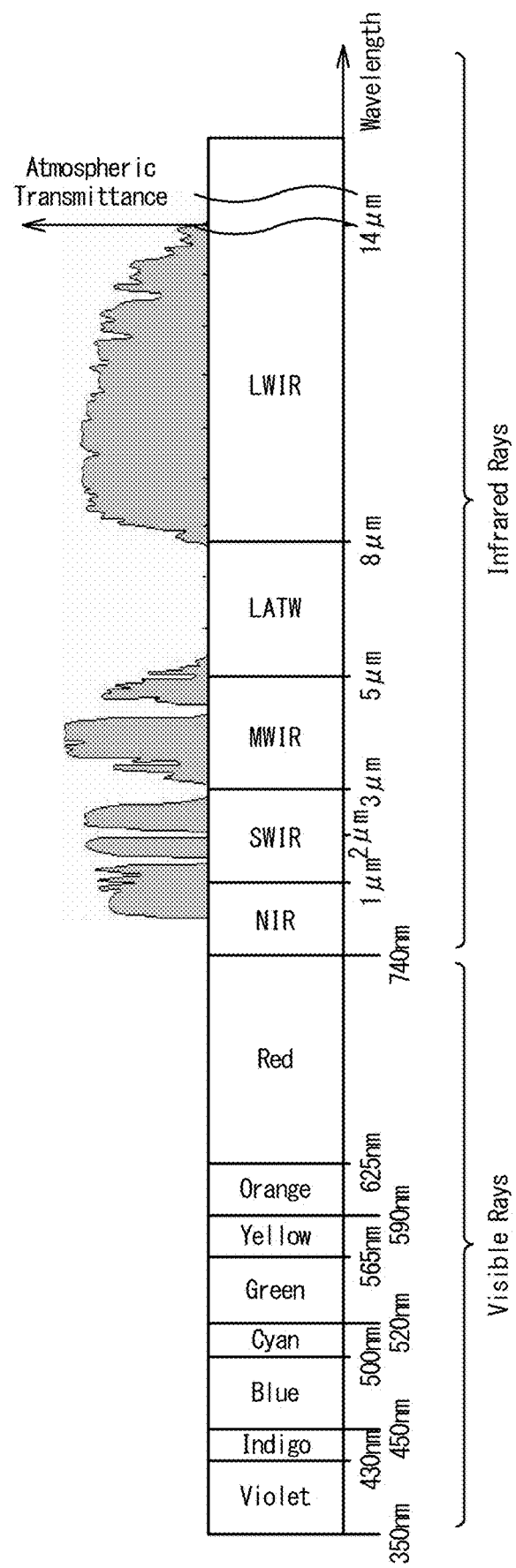
FIG. 3 is a diagram that shows an example of visible light band and infrared band used in an embodiment.

Visible light band and infrared band that are used in the present embodiment will be described with reference to FIG. 3. FIG. 3 is a diagram that shows an example of visible light band and infrared band used in an embodiment.

The horizontal axis in FIG. 3 shows wavelength of light. Light with a wavelength from approximatively 350 nm to approximatively 740 nm is generally called visible rays and can be recognized by human beings as a color from red to violet. Light with a wavelength longer than approximatively 740 is generally called infrared rays and cannot be seen by eyes of human beings. In addition, although it is omitted in FIG. 3, light with a wavelength shorter than approximatively 350 nm is generally called ultraviolet rays and neither cannot be seen by eyes of human beings.

The band of infrared rays is classified by a wavelength or a frequency thereof. Although there are various theories on how to classify, herein it will be classified as following. That is, infrared rays with a wavelength from 0.74 microns to 1 micron will be called "near-infrared (NIR)". Infrared rays with a wavelength from 1 micron to 3 microns will be called "short-wavelength infrared (SWIR)". Infrared rays with a wavelength from 3 microns to 5 microns will be called "mid-wavelength infrared (MWIR)". Infrared rays with a wavelength from 8 microns to 14 microns will be called "long-wavelength infrared (LWIR)" or "thermal infrared (TIR)". Although it is omitted in FIG. 3, light with a wavelength longer than 14 microns will be called "far infrared (FIR)".

In FIG. 3, an atmospheric transmittance of infrared rays is shown on the vertical axis. It is known that it is difficult to use infrared rays with wavelength from 5 microns to 8 microns to observe ground surface from an artificial satellite for example because the infrared rays of this band have a low atmospheric transmittance and are easily absorbed by the atmosphere. This band is called "low atmospheric transmittance window (LATW)" for convenience. Therefore, in the present embodiment, infrared rays with a wavelength of 5 microns or less and infrared rays with a wavelength of 8 microns or more are preferentially used. Specifically, SWIR, MWIR and LWIR may be used. It should be noted that a use of SWIR is effective, for example, to examine an amount of minerals, silicon and the like in soil. By examining the amount of minerals, silicon and the like in soil, it can be determined whether this soil is suitable for rice cultivation or not, for example.

Figure 4A:
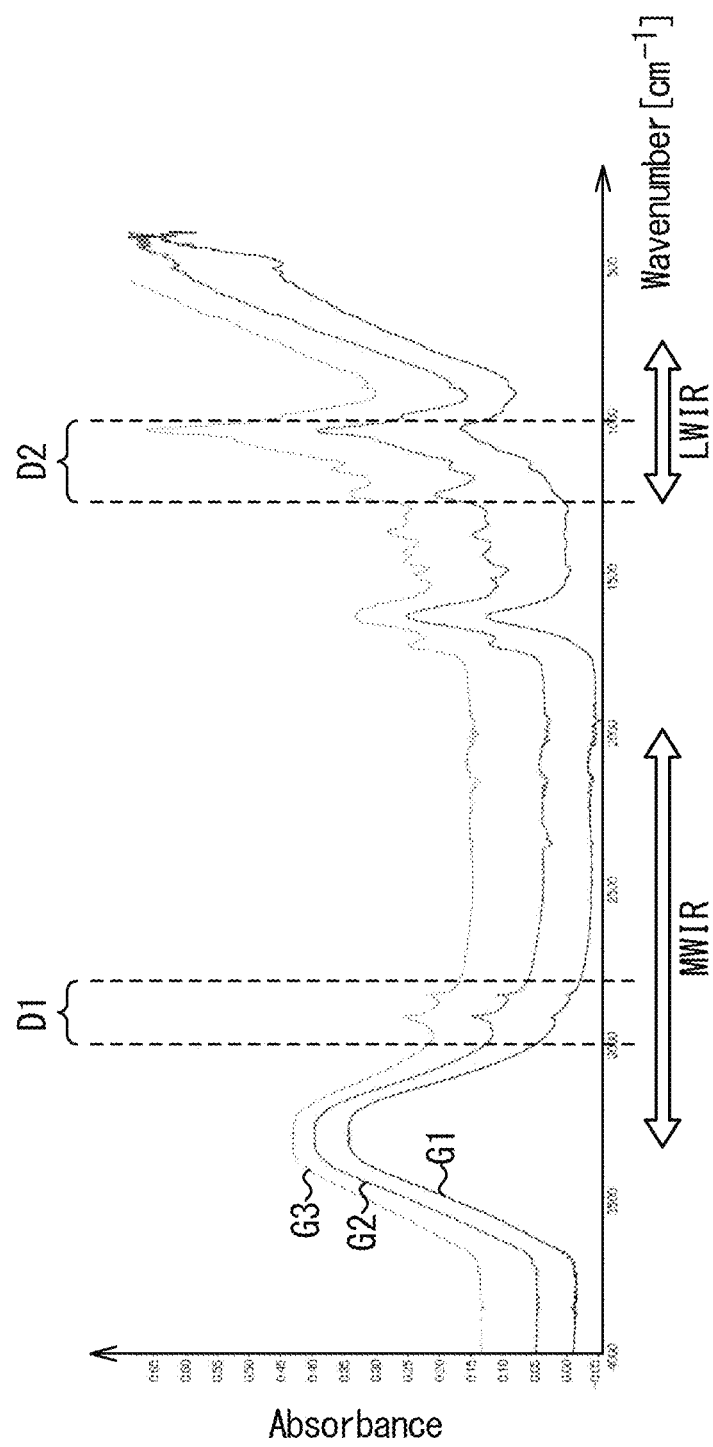
FIG. 4A is a graph to compare infrared absorption spectral characteristics of rice plant and weeds acquired in an embodiment.
Figure 4B:
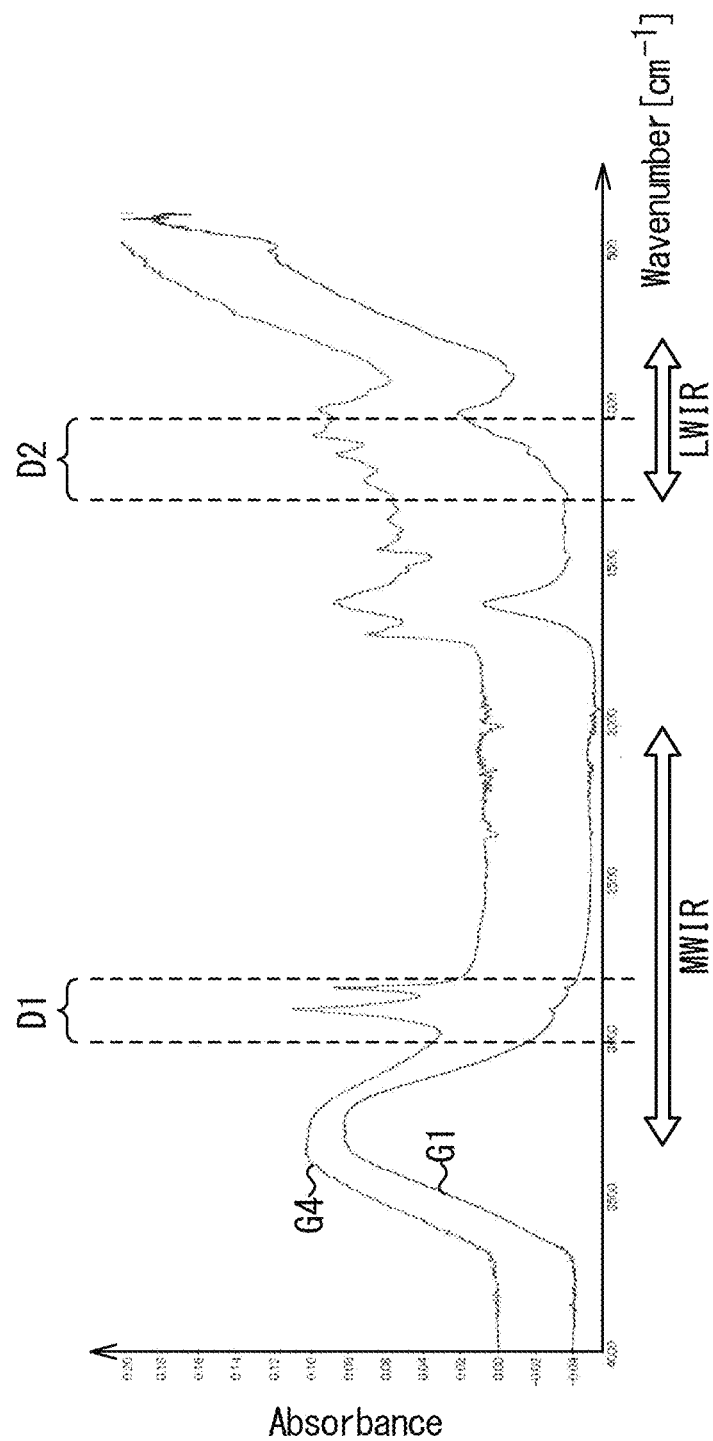
FIG. 4B is a graph to compare infrared absorption spectral characteristics of rice plant and soy acquired in an embodiment.

It will be described with reference to FIGS. 4A and 4B that species of a plant can be determined based on a measurement result of spectral characteristics in MWIR and/or LWIR of light derived from the plant. FIG. 4A is a graph to compare infrared absorption spectral characteristics of rice plant and weeds acquired in an embodiment. FIG. 4B is a graph to compare infrared absorption spectral characteristics of rice plant and soy acquired in an embodiment. The infrared absorption spectral characteristics that are shown in graphs of FIGS. 4A and 4B can be obtained by a Fourier transform of the measurement result. Herein, in frequency regions of infrared rays, not only LATW but also a part of MWIR, a part of LWIR, FIR and the like, sunlight does not reach the ground. Therefore, in those frequency regions, a light source of corresponding infrared band can be used in laboratory to measure absorption characteristics of plants. In other words, it is difficult in those frequency regions to directly measure infrared absorbance of plants by outdoor remote sensing. However, it is possible to obtain a waveform similar to the absorbance by measuring spectral characteristics of radiated light derived from the plants by remote sensing. This is because, as described later, absorbance and radiation of light by plants have same characteristics. It should be noted that sunlight reflection characteristics of plants in SWIR, NIR, visible rays and ultraviolet rays can be measured by remote sensing.

FIG. 4A shows a first spectrum G1, a second spectrum G2 and a third spectrum G3. Common to the first spectrum G1, the second spectrum G2 and the third spectrum G3, the horizontal axis indicates a wavenumber and the vertical axis indicates an absorbance. The first spectrum G1 indicates an absorbance of rice plant, the second spectrum G2 indicates an absorbance of *Cyperus microiria* and the third spectrum G3 indicates an absorbance of *Schoenoplectiella hotarui*.

In the example of FIG. 4A, the first spectrum G1 of rice plant, the second spectrum G2 of *Cyperus microiria* and the third spectrum G3 of *Schoenoplectiella hotarui* have parts of which waveforms are similar to each other and parts in which characteristic differences are observed in each other's waveforms. For example, in a band of MWIR, specifically in a first band D1 shown in FIG. 4A, that is, a band with a wavenumber from approximatively 2800 $cm^{-1}$ to approximatively 3000 $cm^{-1}$, a height of a local peak in the waveform is relatively low in the first spectrum G1 of rice plant and relatively high in the second spectrum G2 of *Cyperus microiria* and the third spectrum G3 of *Schoenoplectiella hotarui*. In addition, similar difference is observed in the second band D2 shown in FIG. 4A, that is, a band with a wavenumber from approximatively 1000 $cm^{-1}$ to approximatively 1250 $cm^{-1}$, too. By creating a database of such waveform features and by mathematically defining a similarity to an arbitrary waveform, identification of plant species becomes possible. This database may be created based on results of measurement carried out in laboratories, for example.

*Cyperus microiria* and *Schoenoplectiella hotarui* are weeds that look like rice plant. Even if *Cyperus microiria* and *Schoenoplectiella hotarui*, that are undesired weeds, are growing in a rice field to cultivate rice plant, they may be difficult to be distinguished just by their appearance. Therefore, in conventional agriculture, a method of spraying a special agricultural chemical that selectively removes weeds and has a little influence on rice plant throughout a rice field is known. However, such special agricultural chemical is relatively expensive, a relatively large amount of agricultural chemical is required to spray throughout a rice field and work costs and the like for spraying a relatively large amount of agricultural chemical are also required. Furthermore, by distinguishing weeds and selectively spraying agricultural chemical on area where weeds are present by use of so-called drones for example, a problem of imprudently contaminating soil in area where no weeds exist with the agricultural chemical can be suppressed from occurring.

In the present embodiment, by comparing spectral characteristics of radiated light of infrared rays measured by the hyperspectral camera 71, specifically in MWIR band and/or LWIR band thereof, an area of a rice field where rice plant is growing and an area of the rice field where weeds are growing can be clearly distinguished. As a result, for example, an agricultural chemical that removes weeds can be sprayed just on areas where weeds are growing. Furthermore, if an agricultural chemical can be sprayed on the area where rice plant is not growing, even an agricultural chemical that has some influence on rice plant may be used to remove weeds. Therefore, compared with the conventional method described above, costs for removing weeds can be significantly saved and in addition unnecessary contamination of soil with an agricultural chemical can be suppressed.

FIG. 4B shows the first spectrum G1 of rice plant same as FIG. 4A and a fourth spectrum G4 of soy. In FIG. 4B, similarly to FIG. 4A, the horizontal axis indicates the wavenumber and the vertical axis indicate the absorbance. Also, by comparing rice plant and soy, when focusing on MWIR band, specifically the first band D1 therein, and LWIR band, specifically the second band D2 therein, characteristic differences are observed in their waveforms. In other words, according to the present embodiment, even if a plurality of desired agricultural crops is mixedly growing, by measuring spectral characteristics of radiated light of plants by remote sensing using the hyperspectral camera 71, areas where each of the desired crops are growing can be clearly distinguished.

Figure 5:
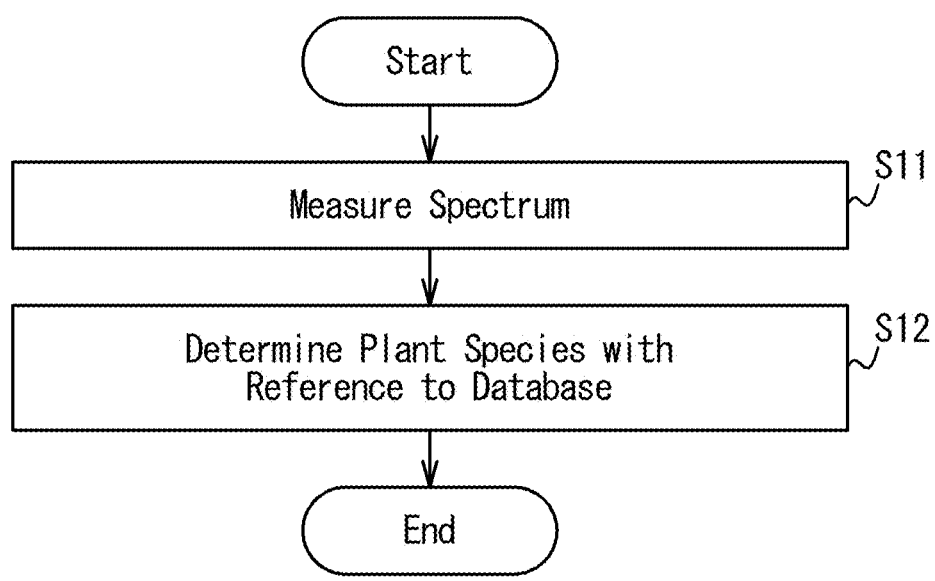
FIG. 5 is a flowchart that shows a configuration example of a precision agriculture support method according to an embodiment.

An operation of the precision agriculture support system 1 according to the present embodiment, that is, a precision agriculture support method according to the present embodiment, will be described with reference to FIG. 5. FIG. 5 is a flowchart that shows a configuration example of a precision agriculture support method according to an embodiment. The flowchart in FIG. 5 is executed by a fully automatic operation and transitions between each of steps included in this flowchart is automatically carried out.

When the flowchart in FIG. 5 starts, the first step S11 is executed. In the first step S11, a spectrum is measured. More specifically, the measuring device 7 carries out a measurement of spectral characteristics of light derived from a vegetation on the ground 8.

Herein, the ground 8 may be, for example, a field or a rice field as a target to support a precision agriculture carried out there. A field or a rice field as a target to support a precision agriculture will be referred to as support target area too in the following. The vegetation of the ground 8 is a set of various plants growing in the support target area and may include, for example, a desired agricultural crop and other weeds.

Light derived from a vegetation is a set of light that the measuring device 7 receives by optically observing plants included in this vegetation. From a perspective of its wavelength, its wavenumber, its frequency and the like, light derived from the vegetation may include all of visible rays, infrared rays and ultraviolet rays.

In addition, from a perspective of its light source, light derived from a vegetation may include: reflected light that is sunlight reflected by plants included in this vegetation; emitted light that is emitted by plants excited by sunlight; and radiated light that is radiated by plants themselves. Reflected light derived from plants may include, for example, components of light irradiating the plants from outside such as sunlight except components thereof absorbed by the plants to carry out photosynthesis. Radiated light of plants follows Kirchhoff's law related to radiant energy. That is, emissivity rate is equal to absorptance rate. Herein, emissivity rate of plants is defined as a value of light energy emitted by the plants by thermal radiation divided by light energy emitted by a black body with temperature same as the plants' one. In addition, absorption rate of plants is defined as a ratio of energy absorbed by the plants to energy of light of an arbitrary wavelength when the plants are exposed to this light.

Temperature measurement of plants may be carried out by measuring spectral characteristics in LWIR band by the hyperspectral camera 71. In general, in remote sensing, as a distance from a measuring device 7 to a measurement target such as plants is relatively long, it may be necessary to carry out complicated corrections to measurement results in order to obtain correct temperature of the measurement target by use of thermal infrared temperature detector 74 that will be described later. That is, for example, it may be necessary to correct effects of temperature, weather conditions and the like of environments that exist between the measuring device 7 and the measurement target. On the other hand, in case of measuring spectral characteristics by use of the hyperspectral camera 71, correct temperature of the measurement target can be obtained by comparing the measured spectral characteristics to theoretical spectrum of black body radiation, without any complicated corrections. Furthermore, some of thermal infrared temperature detectors 74 can obtain temperature distribution map in a planar measurement target area.

Results of measurement of spectral characteristics by the measuring device 7 may be stored in another storage device that is not shown in a format of three-dimensional spectral data as described above, for example.

The second step S12 will be executed after the first step S11. In the second step S12, plants species is determined by referring to a database. More specifically, the plant species determination unit 41 determines whether plants included in the vegetation is the desired agricultural crop or not based on the database of spectrum according species 51 and the result of measurement in the first step S11.

Herein, components of the precision agriculture support system 1 shown in FIG. 1 except the measuring device 7 will be described. The interface 3 carries out detachable connection in order to realize electrical communication with the measuring device 7. In the second step S12, the processing device 4 receives three-dimensional spectral data from the measuring device 7 via the interface device 3 and stores it in the storage device 5 as measured spectral data 52. It should be noted that the interface device 3 may carry out connection with external devices other than the measuring device 7.

The processing device 4 executes programs stored in the storage device 5 and realizes predetermined functions. The storage device 5 stores the programs that the processing device 4 executes, various data that are used when the programs are executed and the like. Herein, the various data stored in the storage device 5 includes the database of spectrum according to species 51. The database of spectrum according to species 51 indicates features that spectral characteristics of arbitrary plants have and it is preferable that those arbitrary plants include desired agricultural crops. In the second step S12, the processing device 4 realizes functions of the plant species determination unit 41 by executing predetermined programs.

The external storage device 6 can read out programs and data from the recording medium 61 and write them in the storage device 5, and conversely read out programs and data from the storage device 5 and write them in the recording medium 61.

When the second step S12 is completed, the flowchart in FIG. 5 ends.

In the precision agriculture support method of the present embodiment, when the desired agricultural crop is rice plant, the rice plant can be identified by determining species of plants growing in the support target area, by executing the flowchart in FIG. 5. In other words, rice plant and weeds such as *Cyperus microiria* and *Schoenoplectiella hotarui* can be accurately distinguished by optical remote sensing using the hyperspectral camera 71.

Although in the above a case in which the desired agricultural crop is rice plant is described, the present invention is not limited to this case. That is, a precision agricultural support system 1 similar to the present embodiment may be used for agricultural crop other than rice plant and a precision agricultural support method similar to the present embodiment can be realized.

Second Embodiment

In the present embodiment, reduce of a desired agricultural crop yield is suppressed by measuring how the desired agricultural crop is growing, discovering abnormality occurrence in an early stage based on a result of this measurement and carrying out necessary treatment in a timely manner to eliminate the abnormality. In other words, early warning is carried out in order to suppress reduce of agricultural crop yield.

Figure 6:
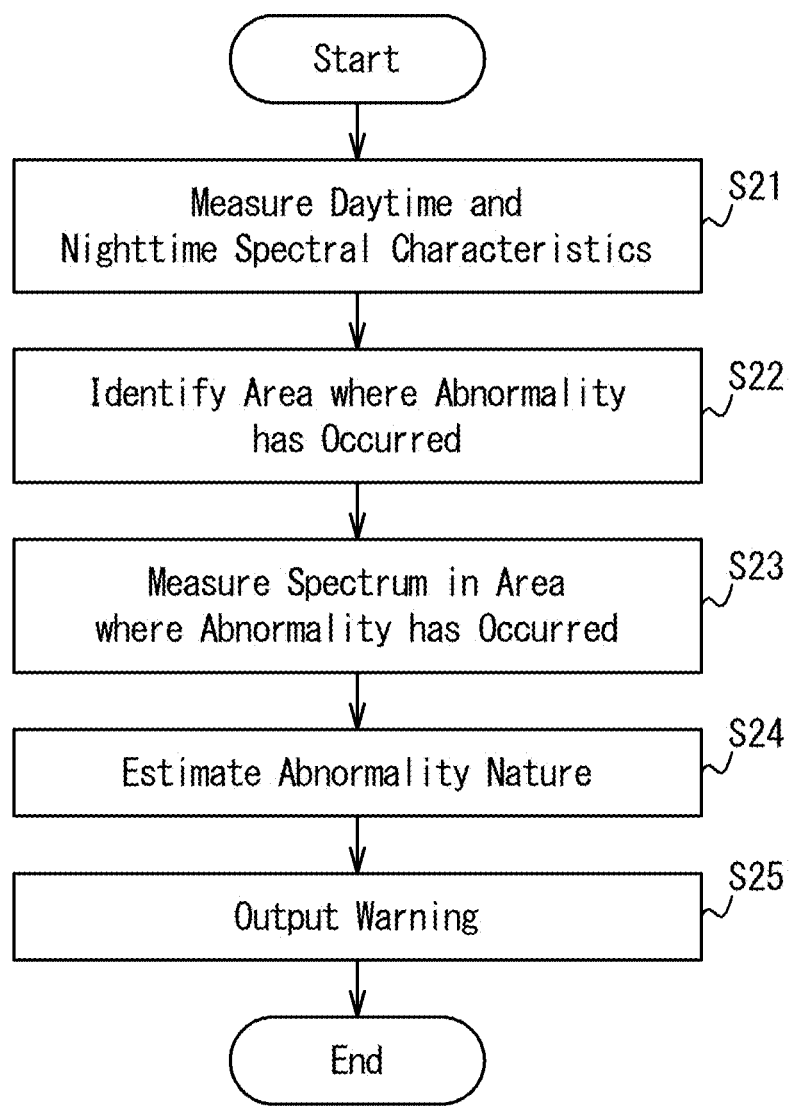
FIG. 6 is a flowchart that shows another configuration example of a precision agriculture support method according to an embodiment.

The precision agriculture support method according to the present embodiment will be described with reference to FIG. 6. FIG. 6 is a flowchart that shows another configuration example of a precision agriculture support method according to an embodiment. The flowchart in FIG. 6 is executed by a fully automatic operation and transitions between each of steps included in this flowchart is automatically carried out.

When the flowchart in FIG. 6 starts, the first step S21 is executed. In the first step S21, the measuring device 7 measures daytime and nighttime spectral characteristics of a vegetation in a support target area. Herein, the measuring device 7 can measure temperature of plants with high accuracy, specifically by measuring by the hyperspectral camera 71 radiated light that the plants themselves included in the vegetation radiate. In the first step S21, spectral characteristics of radiated light of plants, specifically components thereof called MWIR with a wavelength from approximatively 3 microns to approximatively 5 microns and components thereof called LWIR or TIR with a wavelength from approximatively 8 microns to approximatively 14 microns, may be measured. Or, the measuring device 7 may be further provided with a thermal infrared temperature detector 74. In this case, it is preferable that the precision agriculture support system 1 is further provided with a correction unit 45 that corrects influence of environment existing between the thermal infrared temperature detector 74 and the vegetation on a measurement result of temperature. The correction unit 45 may realize the functions thereof by an execution of a predetermined program by the processing device 4, for example. It should be noted that the thermal infrared temperature detector 74 and the correction unit 45 can be omitted in case of measuring plant temperature by use of the hyperspectral camera 71. In order to show this, the thermal infrared temperature detector 74 and the correction unit 45 are drawn by broken lines in FIG. 1. In any case, in the first step S21, temperature of vegetation in support target area can be measured by the measuring device 7 mounted on flying object such as a drone, an aircraft, a balloon or an artificial satellite and the distribution map of temperature of the vegetation can be generated by the processing device 4 based on results of this measurement.

Plants in healthy state try to keep their temperature constant. That is, during daytime or the like, when temperature of the surroundings such as soil, air and the like rises due to sunlight, plants try to adjust their temperature so that it does not rise too much, try to lower their temperature below the temperature of the surroundings, for example, by transpiration which consists of opening stomata and releasing water vapor. On the contrary, during nighttime or the like, when temperature of the surroundings decreases, plants try to raise their temperature above the temperature of the surroundings by closing stomata and by respiration. However, plants may become in a stressed state with deteriorating health due to some reason and their ability of adjusting their temperature may be reduced. In other words, states of plants can be estimated by measuring temperature of the plants.

Figure 7A:
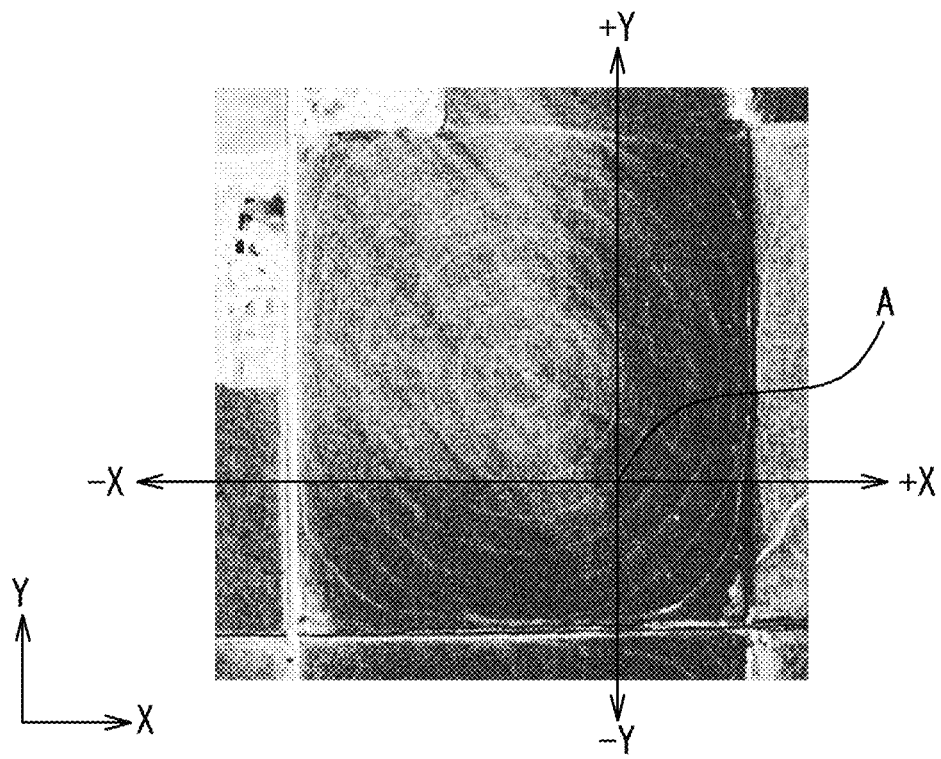
FIG. 7A is a diagram that shows an example of measurement result of nighttime spectral characteristics of an agricultural crop in an embodiment.
Figure 7B:
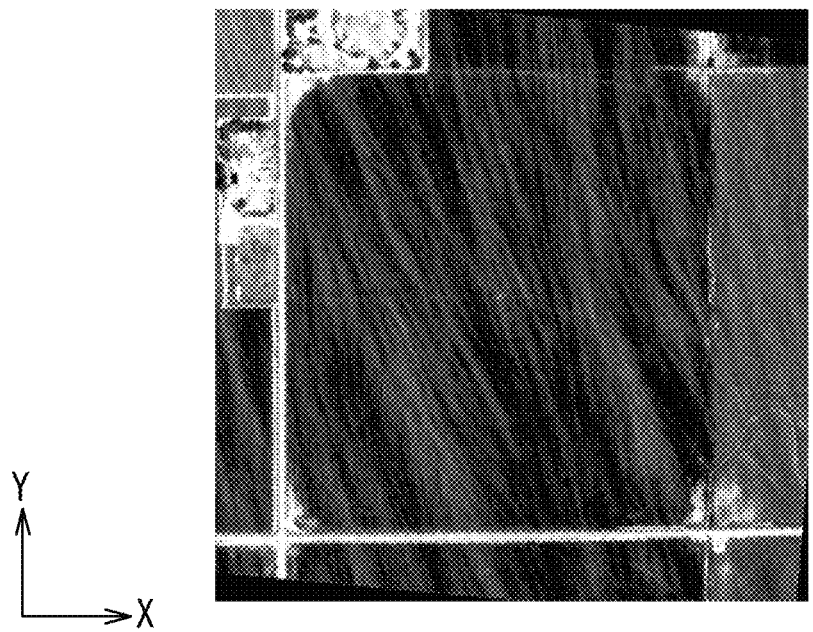
FIG. 7B is a diagram that shows an example of measurement result of daytime spectral characteristics of the agricultural crop shown in FIG. 7A.

An example of measuring plants temperature will be described with reference to FIGS. 7A and 7B. FIG. 7A is a diagram that shows an example of measurement result of nighttime spectral characteristics of an agricultural crop in an embodiment. FIG. 7B is a diagram that shows an example of measurement result of daytime spectral characteristics of the agricultural crop shown in FIG. 7A.

At first, in the example in FIG. 7A, agricultural crops are uniformly growing in a field that has an approximate square shape. However, temperature distribution of the agricultural crops cultivated in this field is not uniform and can be classified into a first group with higher temperature and a second group with lower temperature. The first group is represented by brighter colors and is concentrated in an area of the square field shown in FIG. 7A in approximatively ⅔ part in left side (−X side) and approximatively ⅔ part in upper side (+Y side) by referring to point A. In addition, the second group is represented by darker colors and is concentrated in the remaining area.

Therefore, it can be read from FIG. 7A that temperature of the agricultural crops of the first group is kept warmer compared to the agricultural crops of the second group in the nighttime when the soil is cooled because sunlight does not reach. In other words, the agricultural crops of the second group have lower biomass density compared to the agricultural crops of the first group or has stress (problems) such as illness.

Next, in the example of FIG. 7B, the temperature distribution of the agricultural crops in the field same as FIG. 7A is different from the example of FIG. 7A. In other words, the temperature distribution of the same plants is different in daytime and nighttime. In FIG. 7B, the first group with higher temperature is represented by brighter colors and in contrary the second group with lower temperature is represented by darker colors. It should be noted that the distribution in FIG. 7B is mottled and cannot be simply compared with the distribution in FIG. 7A. That is, individuals that cannot adjust temperature in both daytime and nighttime, individuals that cannot adjust temperature in daytime only, individuals that cannot adjust temperature in nighttime only and individuals that can adjust temperature in daytime and nighttime are mixed in the field of FIGS. 7A and 7B. In other words, those individuals may have stresses of different causes.

In the first step S21, there is a case in which it is difficult to generate a distribution map of vegetation temperature. This is a case in which, for example, it is not common to mount the hyperspectral camera 71 adapted to long-wavelength infrared band on a drone because of its heavy weight and its expensive price. In such a case, a distribution map of features of spectral characteristics may be generated instead of distribution map of vegetation temperature. For example, instead of a hyperspectral camera 71 adapted to long-wavelength infrared band, a simpler hyperspectral camera 71 adapted to a band from visible rays to near-infrared rays may be used. In this case, spectral characteristics obtained by the hyperspectral camera 71 from visible rays to near-infrared rays can be analyzed and a distribution map of feature that represent the result thereof can be generated.

It should be noted that the measurement of the spectral characteristics in the first step S21 is carried out in order to identify an area where abnormality has occurred in the following second step S22. Therefore, it is preferable to measure the spectral characteristics in the entire support target area.

The second step S22 is executed after the first step S21. In the second step S22, the precision agriculture support system 1 identifies areas where an abnormality is occurring to plants. More specifically, the abnormality area identification unit 42 of the precision agriculture support system 1 identifies areas, where an abnormality is occurring to plants, of the ground 8 as the support target area, based on the result of measurement of spectral characteristics in the first step S21. The function of the abnormality area identification unit 42 may be realized by an execution of a predetermined program by the processing device 4.

In this program, for example, an image processing of improving signal to noise ratio (S/N ratio) by reducing noise in distribution map generated in the first step S21 may be carried out. In addition, in order to elucidate a cause of a stress that the plants are undergoing, this program carries out calculation of a special algorithm by combining results of measurements in a plurality of bands included in wavelength range from visible rays to long-wavelength infrared rays and compares the result of this calculation with various databases by collation. Herein, the various databases may be public databases and may be proprietary databases. By doing so, a stress that plants are undergoing can be discovered in an earlier stage, and causes, countermeasures and the like thereof can be provided to farmers.

By further analyzing the analysis results of data obtained by measurements combined with experimental results, historical production data in the agricultural land of the support target area and the like, information practical for farmers to manage the agricultural land, up-to-date and more complete can be provided.

Figure 7C:
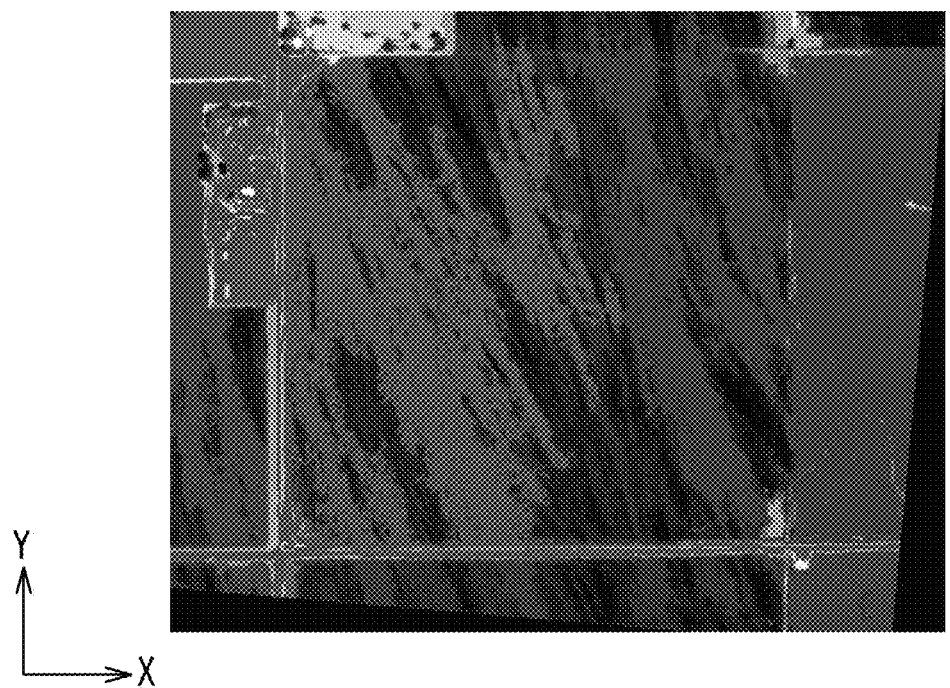

An area where an abnormality is occurring to plants will be described with reference to FIG. 7C. FIG. 7C is a diagram in which FIG. 7A and FIG. 7B are combined. FIG. 7C can be obtained by combining FIGS. 7A and 7B after making respective changes as follows. That is, in FIG. 7B, as it can be considered that plants in an area of higher temperature in daytime have more stress, colors of FIG. 7B are changed so that the colors in this area match with the colors of the second group in nighttime shown in FIG. 7A.

In the example of FIG. 7C, among the plants growing in the approximate square field, individuals in areas represented by brighter colors have relatively small stress and individuals in areas represented by darker colors have relatively large stress on the contrary. Herein, it is visualized that, in fact, areas of relatively large stress are mixed in the area supposed that nighttime stress is relatively small. On the contrary, it is also visualized that, in fact, areas of relatively small stress are mixed in the area supposed that nighttime stress is relatively large. In addition, areas of relatively large stress in daytime and nighttime are represented by darkest colors, areas of relatively small stress in daytime and nighttime are represented by brightest colors and areas of relatively large stress in one of daytime or nighttime are represented by intermediate density of colors. For example, although the first group in FIG. 7A was considered to be an area of relatively small stress, stripes with dark colors that indicates relatively large stress can be slightly seen, in fact. As described above, stress of not being able to adjust temperature in nighttime only, stress of not being able to adjust temperature in daytime only and stress of not being able to adjust temperature in both daytime and nighttime can be distinguished based on nighttime temperature measurement result such as in FIG. 7A, daytime temperature measurement result such as in FIG. 7B and combined data such as in FIG. 7C.

The third step S23 is executed after the second step S22. In the third step S23, the measuring device 7 measures spectrum in area where abnormality has occurred.

It should be noted that, although in the first step S21 spectral characteristics was measured in all the support target area in order to identify areas where abnormality has occurred, spectral characteristics may be measured only in the identified area where abnormality has occurred in the third step S23. This is because the measurement of spectral characteristics in the third step S23 is carried out in order to estimate a nature of the abnormality in the following fourth step S24.

The fourth step S24 is executed after the third step S23. In the fourth step S24, the precision agriculture support system 1 estimates an abnormality nature. More specifically, the abnormality nature estimation unit 43 of the precision agriculture support system 1 estimates a nature of the abnormality of which area of occurrence was identified in the second step S22 based on spectral characteristics of reflected light that is reflected by the plants, among spectral characteristics measured in the third step S23. The function of the abnormality nature estimation unit 43 may be realized by an execution of a predetermined program by the processing device 4.

The abnormality nature estimation unit 43 refers to the abnormality database 53 stored in the storage device 5 and estimates a nature of the abnormality corresponding to the feature that the result of measurement of the spectral characteristics in the third step S23 has. In other words, the abnormality database 53 may include data indicating relationship between types of abnormality that may occur to plants and feature of spectral characteristics of plants to which the abnormality has occurred.

The firth step S25 is executed after the fourth step S24. In the fifth step S25, the precision agriculture support system 1 outputs a warning. More specifically, the warning unit 44 of the precision agriculture support system 1 outputs a warning based on a result of the estimation of the nature of abnormality in the fourth step S24. A specific content of this warning may be, for example, informing occurrence of abnormality with the estimated nature and may be, more preferably, suggesting to carry out a countermeasure against occurring abnormality. Data indicating a countermeasure against abnormality may be, for example, included in the abnormality database 53 so that the warning section 44 can read out. Furthermore, the abnormality database 53 may include nature, feature and countermeasure related to an abnormality in a state of association with each other.

As a detailed method of outputting a warning, an explanation including letters, numbers, geographic information and the like may be indicated in writing, may be visually shown by optical device such as a display, a lamp or the like that is not shown in drawings, and may be aurally given by a sound device such as a speaker, a buzzer or the like that is not shown in drawings.

Figure 8A:
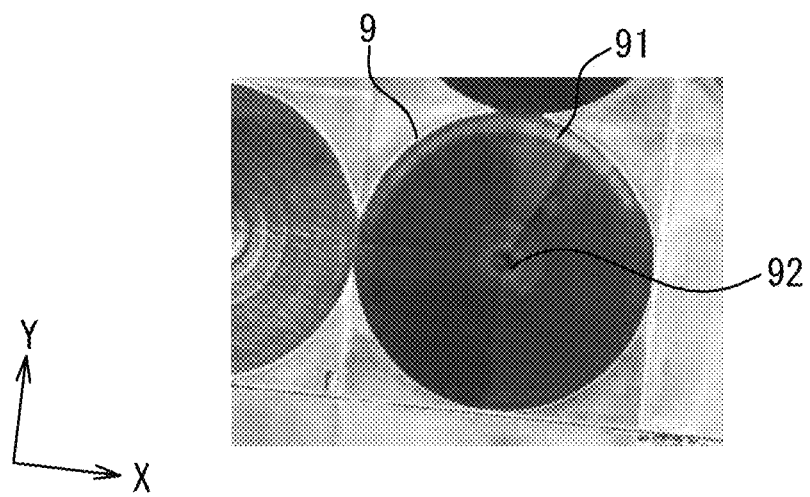
FIG. 8A is a diagram that shows an example of measurement result of spectral characteristics in a circular farm growing corn in an embodiment.
Figure 8B:
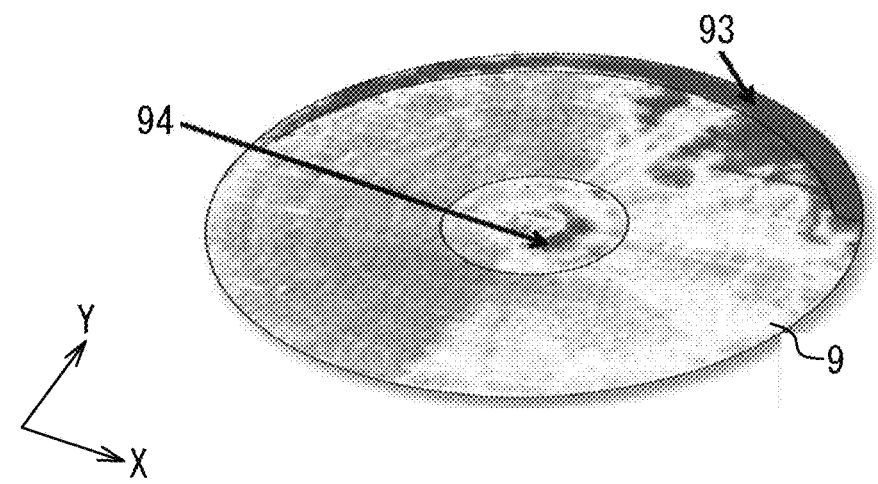
FIG. 8B is a diagram that shows an example of crop yield on the circular farm shown in FIG. 8A.

A case in which a crop yield in an area where an occurrence of abnormality has been detected during the growth of the crop actually became lower compared to crop yield in an area where no occurrence of abnormality has been detected will be described with reference to FIGS. 8A and 8B. FIG. 8A is a diagram that shows an example of measurement result of spectral characteristics in a circular farm 9 with corn in an early stage of growing in an embodiment. FIG. 8B is a diagram that shows an example of crop yield on the circular farm 9 shown in FIG. 8A.

In the case of FIG. 8A, two abnormality areas 91 and 92 are detected in the circular farm 9. The first abnormality area 91 is located in a peripheral area of the circular farm 9. In addition, the second abnormality area 92 is located in a center area of the circular farm 9. However, because height of corn in early stage of growing is still low and a density thereof is still low, it may be considered that a temperature distribution shown in FIG. 8A is closer to a temperature distribution of soil than a temperature distribution of corn itself. In FIG. 8A, temperature of the abnormality areas 91 and 92 with lighter colors is slightly higher compared to other areas with deeper color. Difference of temperature between both areas is within 1 degree Celsius. Although such a difference is difficult to understand visually, it can be considered that a reason why the temperature is relatively high is because water retention of the soil is poor and sprinkled water is not kept enough.

As shown in FIG. 8A, by analyzing measurement result of the spectral characteristics of all the circular farm 9, it has been found that temperature is high and water is insufficient in the abnormality areas 91 and 92. Then, as shown in FIG. 8B, it has been found that, when agricultural crops in the circular farm 9 are harvested, crop yield is lower in two areas than in other areas. It has been verified that those two low yield areas 93 and 94 match to abnormality areas 91 and 92 where water was insufficient, respectively. That is, it can be estimated that local water shortage shown in FIG. 8A was a cause of local reduction of crop yield shown in FIG. 8B.

This case shows that it is possible to detect an occurrence of abnormality that is a cause of a reduction of yield of agricultural crop at a timing during the growth of the agricultural crop. In addition, this case also shows a possibility in that reduce of yield of the agricultural crop would be suppressed if appropriate countermeasure was carried out at a timing of detection of the abnormality occurrence.

In the case of FIGS. 8A and 8B, because insufficient water supply due to partial failure of sprinkler, poor water retention of soil and the like can be considered as a cause of water shortage, repairing the sprinkler, covering the soil surface with a soil of good water retention and the like can be considered as a countermeasure, for example.

As described above, the precision agriculture support system 1 and the precision agriculture support method according to the present embodiment can suppress reduce of yield of agricultural crop by carrying out an early warning. That is, by discovering an occurrence of abnormality of growing agricultural crop in an early stage and by suggesting effective countermeasures in time for harvesting the agricultural crop, growing state of the agricultural crop can be brought to a healthier state and a final crop yield can be brought closer to an original expected value. In other words, reduce of crop yield can be suppressed.

An early warning will be described in more detail. As described above, when an abnormality occurs in a plant, its ability of adjusting temperature of itself may be reduced. As an example, there is a case in which it occurs an abnormality in that temperature of a plant decreases too much in nighttime even by closing stomata although the plant is able to appropriately adjust its temperature in daytime. On the contrary, there is also a case in which it occurs an abnormality in that temperature rises too much in daytime even by opening stomata although the plant is able to appropriately adjust its temperature in nighttime. Plants to which such abnormality occurs will have stress. In the present embodiment, because such abnormality can be detected at a timing of the first step S21 or the second step S22, for example, the third step S23 and the fourth step S24 may be omitted, that is, a warning in an early stage may be outputted in the fifth step S25 before estimating or without estimating a cause of stress of the plants.

As causes of stress of plants, there are insufficiency of fertilizer (nitrogen, phosphorus and the like), shortage of water, illness, pests and the like. Based on which of daytime or nighttime an abnormality occurs, or, with reference to the abnormality database 53, a cause of stress of the plant may be estimated. In such a case, the abnormality database 53 may further include data indicating relationship between a type of abnormality that may occur to the support target area and a feature of temperature in daytime and nighttime in the support target area where the abnormality has occurred. As an example, there is a case in which, due to shortage of water, although temperature of plants does not drop enough in daytime even if the plants try transpiration by opening stomata, the plants are brought to a normal state in nighttime. The warning unit 44 may output warning based on the abnormality database 53, temperature measurement result and abnormality area detection result.

When the fifth step S25 is complete, the flowchart in FIG. 6 ends. Or, after the fifth step S25 is complete, the flowchart in FIG. 6 may be executed again from the first step S21.

In the flowchart in FIG. 6, if no occurrence of abnormality is discovered in the second step S22, the first step S21 may be executed again instead of proceeding to the third step S23. In other words, the first step S21 and the second step S22 may be repeated until an occurrence of abnormality is discovered. This repetition may be regularly or irregularly carried out in accordance with growing state of the agricultural crop.

The flowchart in FIG. 5 to be executed to determine plant species and the flowchart in FIG. 6 to be executed to identify an area where abnormality is occurring and to estimate a nature of the abnormality can be executed in any order. Or, parts or all of both flowcharts may be executed at a same time in parallel.

Although the invention made by the inventors has been described above in detail based on embodiments, it is needless to assert that the present invention is not limited by the above described embodiments and that various changes can be made within a scope of the gist. In addition, each feature described in above embodiments can be freely combined within a technically consistent range.

It should be noted that the present application claims priority based on Japanese patent application No. 2019-105490 filed on Jun. 5, 2019 and incorporates herein all disclosure thereof by reference.

DESCRIPTION OF SYMBOLS

1 Precision agriculture support system
2 Bus
3 Interface device
4 Processing device
41 Plant species determination unit
42 Abnormality area identification unit
43 Abnormality nature estimation unit
44 Warning unit
45 Correction unit
5 Storage device
51 Database of spectrum according to species
52 Measured spectral data
53 Abnormality database
6 External storage device
61 Recording medium
7 Measuring device
701 Travelling direction
702 Array direction
703 Instantaneous field of view
704 Unit field of view
71 Hyperspectral camera
72 Positioning device
73 Moving device
74 Thermal infrared temperature detector
8 Ground
801 Unit length
802 Observation width
9 Circular farm
91 Abnormality area
92 Abnormality area
93 Low yield area
94 Low yield area

The invention claimed is:
1. A precision agriculture support system comprising:
a measuring device configured to measure a first spectral characteristic of light derived from a vegetation in a support target area;
a storage device configured to store a database of spectra according to species that shows a feature a spectral characteristic of a desired crop has; and
a plant species determining unit configured to determine whether a plant included in the vegetation is the desired crop or not based on the database of spectra according to species and a measurement result of the first spectral characteristic,
wherein the desired crop includes rice plants,
wherein the light includes at least:
emitted light that is emitted by the plant excited by sunlight; and
radiated light that is radiated by the plant itself, wherein the measuring device is further configured to measure daytime spectral characteristics of the support target area and nighttime spectral characteristics of the support target area, and wherein the precision agriculture support system further comprises:

an abnormality area identification unit configured to identify an abnormality area where an abnormality, in that an ability of the plant to adjust temperature of the plant itself is reduced, is occurring among the support target area based on at least a first component of Long-Wavelength InfraRed (LWIR) with a wavelength from 8 microns to 14 microns included in the radiated light of a first measurement result of the daytime spectral characteristics and a second component of the LWIR included in the radiated light of a second measurement result of the nighttime spectral characteristics; and a warning unit configured to perform an early warning, based on an identification result of the abnormality area, in order to suppress reduction of agricultural crop yield.

2. The precision agriculture support system according to claim 1, wherein the measuring device comprises a hyperspectral camera configured to optically observe the support target area and measure a spectral characteristic related to a predetermined wavelength range including at least a part of visible light, near-infrared rays, short-wavelength infrared rays, mid-wavelength infrared rays and long-wavelength infrared rays.

3. The precision agriculture support system according to claim 1, wherein the plant species determining unit is configured to carry out the determination based on a feature included in a mid-wavelength infrared band with wavelength from 3 microns to 5 microns among the measurement result of the first spectral characteristic.

4. The precision agriculture support system according to claim 1, wherein the plant species determining unit carries out the determination based on a feature included in a long-wavelength infrared band with a wavelength from 8 microns to 14 microns among the measurement result of the first spectral characteristic.

5. The precision agriculture support system according to claim 1, wherein the storage device is further configured to store an abnormality database that shows a relationship between a type of abnormality that may occur to the support target area and a feature that daytime and nighttime spectral characteristics of the support target area where an abnormality has occurred have, and wherein the measuring device is further configured to measure daytime and nighttime spectral characteristics of the support target area, wherein the abnormality area identification unit is further configured to identify an abnormality area where an abnormality is occurring among the support target area based on the measurement result of the spectral characteristic; and the warning unit is further configured to output a warning based on the abnormality database, the measurement result of the spectral characteristic and the identification result of the abnormality area.

6. The precision agriculture support system according to claim 1, wherein the measuring device is further configured to measure a second spectral characteristic of light derived from a vegetation of the abnormality area among the vegetation of the support target area, wherein the storage device is further configured to store an abnormality database that shows a relationship between a type of an abnormality that may occur to a plant and a feature that a spectral characteristic of a plant to which an abnormality has occurred has, and wherein the precision agriculture support system further comprises:

an abnormality nature estimation unit configured to estimate a nature of the abnormality based on the abnormality database and a measurement result of the second spectral characteristics, and wherein the warning unit is further configured to output a warning based on an estimation result of the nature of the abnormality.

7. The precision agriculture support system according to claim 5, wherein the measuring device is configured to measure temperature of the vegetation by measuring the spectral characteristics of light derived from the vegetation of the support target area.

8. The precision agriculture support system according to claim 6, wherein the measurement device is configured to measure temperature of the vegetation by measuring a spectral characteristic of a first band of light derived from the vegetation of the support target area, wherein the first band is included in a set of a mid-wavelength infrared band with a wavelength from 3 microns to 5 microns and a long-wavelength infrared band with a wavelength from 8 microns to 14 microns, wherein the measuring device is configured to measure the second spectral characteristic by measuring a spectral characteristic of a second band of light derived from the vegetation of the abnormality area, and wherein the second band is included in a set of a visible light band with a wavelength from 350 nanometers to 740 nanometers and a near-infrared band with a wavelength from 740 nanometers to 1 micron.

9. The precision agriculture support system according to claim 5, wherein the measuring device further comprises a thermal infrared temperature detector configured to measure temperature of the vegetation by use of a thermal infrared band, and wherein the precision agriculture support system further comprises a correction unit configured to correct influence of environment existing between the thermal infrared temperature detector and the vegetation on a measurement result of the temperature.

10. A precision agriculture support method including:

preparing a database of spectra according to species that shows a feature a spectral characteristics of a desired crop has;

carrying out a measurement of a spectral characteristic of light derived from a vegetation in a support target area; and determining whether a plant included in the vegetation is the desired crop or not based on the database of spectra according to species and a result of the measurement, wherein the desired crop includes rice plants, wherein the light includes at least:

emitted light that is emitted by the plant excited by sunlight; and radiated light that is radiated by the plant itself, wherein the carrying out the measurement includes:

measuring daytime spectral characteristics of the support target area; and measuring nighttime spectral characteristics of the support target area, wherein the precision agriculture support method further includes:

identifying an abnormality area where an abnormality, in that an ability of the plant to adjust temperature of the plant itself is reduced, is occurring among the support target area based on at least a first component of Long-Wavelength InfraRed (LWIR) with a wavelength from 8 microns to 14 microns included in the radiated light of a first measurement result of the daytime spectral characteristics and a second component of the LWIR included in the radiated light of a second measurement result of the nighttime spectral characteristics; and performing an early warning, based on a result of identification of the abnormality area, in order to suppress reduce of agricultural crop yield.

11. The precision agriculture support method according to claim 10, further including:

preparing an abnormality database that shows a relationship between a type of abnormality that may occur to the support target area and a feature that daytime and nighttime spectral characteristics of the support target area where an abnormality has occurred have;

outputting a warning based on the abnormality database, the first measurement result and second measurement result of the spectral characteristics, and the result of identification of the abnormality area.

12. The precision agriculture support method according to claim 10, further comprising:

preparing an abnormality database that shows a relationship between a type of an abnormality that may occur to a plant and a feature that a result of measurement of a spectral characteristic of a plant to which the abnormality has occurred has;

measuring a second spectral characteristic of light derived from a vegetation in the abnormality area among the support target area;

estimating a nature of the abnormality based on the abnormality database and a measurement result of the second spectral characteristic; and outputting a warning based on an estimation result of the nature of the abnormality.

* * * * *